United States Patent [19]
Thompson et al.

[11] Patent Number: 5,779,685
[45] Date of Patent: Jul. 14, 1998

[54] RETROGRADE CARDIOPLEGIA CATHETER AND METHOD OF USE

[75] Inventors: Thomas C. Thompson, McKinney, Tex.; Andrew S. Wechsler, Richmond, Va.; Tamera L. Clark, McKinney, Tex.

[73] Assignee: Quest Medical, Inc., Allen, Tex.

[21] Appl. No.: 555,767

[22] Filed: Nov. 13, 1995

[51] Int. Cl.$^6$ ............................................. A61M 5/00
[52] U.S. Cl. ............................................. 604/264; 604/96
[58] Field of Search .................. 604/96, 101, 49–53, 604/264, 280, 104, 105, 106; 606/191–197

[56] References Cited

U.S. PATENT DOCUMENTS

| | | |
|---|---|---|
| Re. 35,352 | 10/1996 | Peters . |
| 3,799,173 | 3/1974 | Kamen . |
| 4,210,478 | 7/1980 | Shoney . |
| 4,290,428 | 9/1981 | Durand . |
| 4,413,989 | 11/1983 | Schjeldahl . |
| 4,459,977 | 7/1984 | Pizon . |
| 4,596,552 | 6/1986 | DeVries . |
| 4,610,661 | 9/1986 | Possis . |
| 4,653,514 | 3/1987 | Shapiro . |
| 4,689,041 | 8/1987 | Corday . |
| 4,714,460 | 12/1987 | Calderon . |
| 4,753,637 | 6/1988 | Horneffer . |
| 4,784,638 | 11/1988 | Ghajar . |
| 4,804,358 | 2/1989 | Karcher . |
| 4,850,969 | 7/1989 | Jackson . |
| 5,021,045 | 6/1991 | Buckberg . |
| 5,151,087 | 9/1992 | Jonkman . |
| 5,197,952 | 3/1993 | Marcadis . |
| 5,219,355 | 6/1993 | Parodi . |
| 5,324,260 | 6/1994 | O'Neill . |
| 5,395,331 | 3/1995 | O'Neill . |
| 5,401,244 | 3/1995 | Boykin . |
| 5,411,509 | 5/1995 | Hilal . |
| 5,423,745 | 6/1995 | Todd . |
| 5,443,448 | 8/1995 | DeVries . |
| 5,478,309 | 12/1995 | Sweezer . |
| 5,487,730 | 1/1996 | Maracadis . |
| 5,505,698 | 4/1996 | Booth . |
| 5,548,574 | 8/1996 | Machold . |
| 5,558,644 | 9/1996 | Boyd . |
| 5,584,803 | 12/1996 | Stevens . |
| 5,597,377 | 1/1997 | Aldea . |

FOREIGN PATENT DOCUMENTS

0 249 338 A2   12/1987   European Pat. Off. .

OTHER PUBLICATIONS

Ehud Rudis, et al., "Coronary Sinus Ostial Occlusion During Retrograde Delivery of Cardioplegic Solution Significantly Improves Cardioplegic Distribution and Efficacy," 109 The Journal of Thoracic Cardiovascular Surgery pp. 941–947 (1995). (United States).

Primary Examiner—Michael Buiz
Assistant Examiner—Manuel Mendez
Attorney, Agent, or Firm—Sidley & Austin

[57] ABSTRACT

The present invention relates to a retrograde cardioplegia catheter for the delivery of a cardioplegia solution to a patient's heart during open heart surgery. The catheter includes a flexible, elongated cannula having a proximal and a distal end. The cannula includes at least two lumens, the primary lumen being utilized to deliver cardioplegia solution. Typical of retrograde catheters, a sealing member is positioned and secured about the distal end of the cannula. In contrast to conventional catheters, however, the sealing member is comprised of (i) a thin-walled membrane that defines an interior chamber and (ii) a compressible, resilient form positioned within such chamber to fully support the membrane. The resilient form is in an expanded state when relaxed. The resilient form of the present invention enables the distribution of a consistent, definable force across the surface of the semi-rigid sealing member, whereby the resilient form empowers the sealing member of the present invention to overcome migratory tendencies of air- and fluid-filled sealing members typical of conventional retrograde cardioplegia catheters.

26 Claims, 3 Drawing Sheets

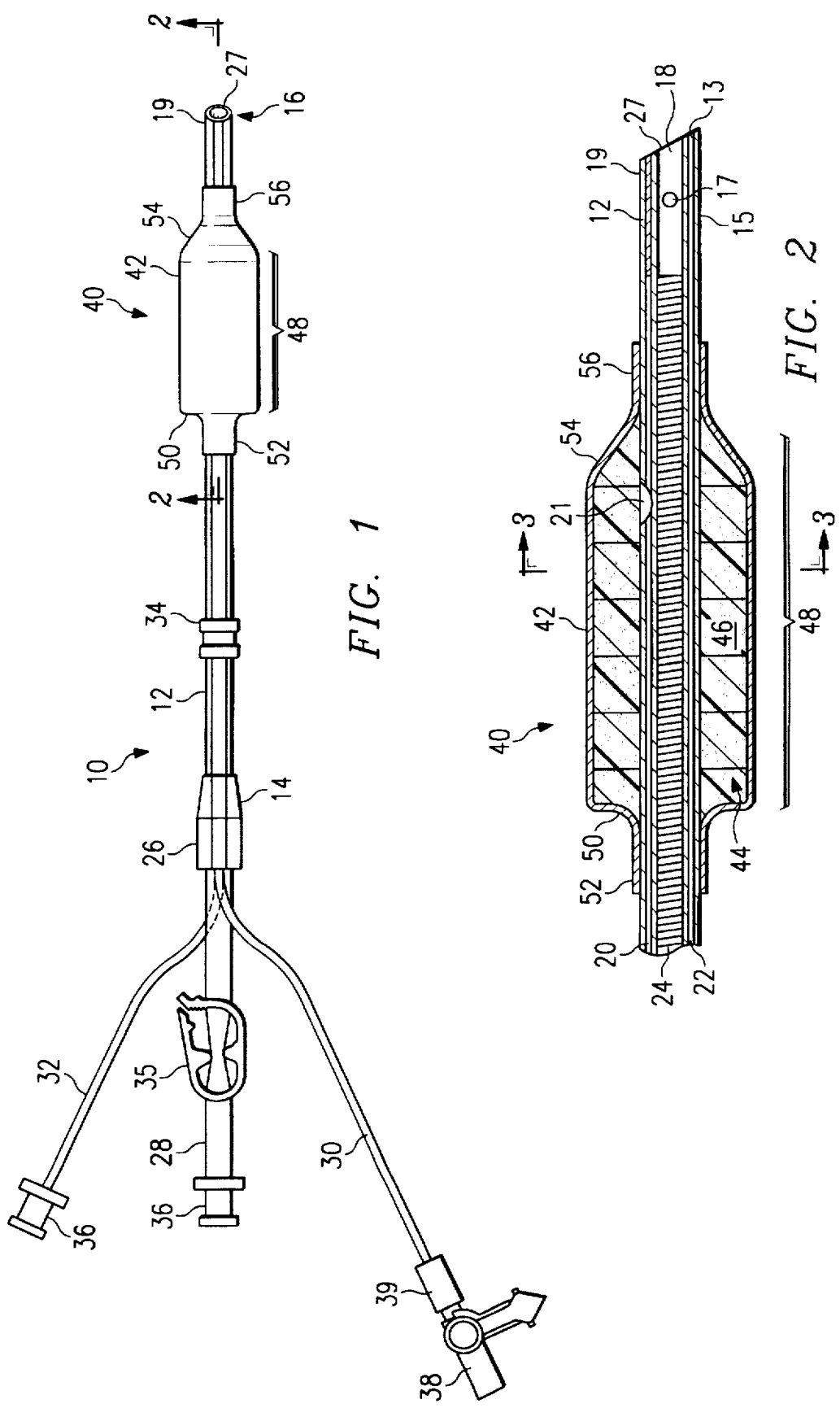

RETROGRADE CARDIOPLEGIA CATHETER AND METHOD OF USE

BACKGROUND OF THE INVENTION

1. Field of the Invention

This invention relates to catheters, and more particularly to a cardioplegia catheter comprising a conforming sealing device and its method of use.

2. Description of Related Art

In cardiac surgical procedures requiring cardiopulmonary bypass, or the diversion of blood to an oxygenator to maintain extracorporeal circulation, the heart is deprived of necessary oxygen and nutrients. To avoid the consequential injury associated with such deprivation, the heart is provided myocardial protection, or the preserving and arresting of the heart, during the open heart procedure.

For myocardial protection, a cardioplegia solution is directed into the heart to: provide essential oxygen and nutrients to the heart tissue; stop the heart's activity; protect the heart during periods of ischemia; and prepare the heart for reperfusion. Cardioplegia solution generally comprises a premixed aqueous saline or glucose crystalloid solution, such crystalloid solution being optionally mixed with oxygenated blood from the patient, to carry various additives necessary to perform the tasks outlined above. As an example, a potassium solution additive is variably introduced to the cardioplegia solution as a means for stopping and maintaining the patient's heart in an arrested state.

Depending upon the requirements of the particular surgery, cardioplegia solution is delivered, either chilled or warm, by a catheter in (i) an antegrade fashion to the aortic root (i.e., through the coronary arteries in a direction consistent with normal blood flow) or (ii) a retrograde fashion to the coronary sinus (i.e., through the coronary veins in a direction opposite of normal blood flow). Any given open heart procedure may utilize both antegrade and retrograde delivery techniques in an effort to achieve the necessary perfusion of the heart tissue. Wherein the heart is subjected to incomplete or inadequate perfusion, immediate or delayed development of myocardial necrosis, the pathologic death of the heart tissue, can occur.

In regard to retrograde delivery, to which the present invention is directed, a balloon catheter is positioned in and delivers cardioplegia to the coronary sinus, wherein the catheter gains access to the coronary sinus through a small incision in the right atrial wall. Conventional balloon catheters are of two general types: manually-filled and self-filling. For the manually-filled variation, a user inflates the sealing balloon with an air-like fluid or a saline solution (hereinafter "inflation fluid") to form a closed interface, or seal, between the balloon surface and the vessel wall. Common to many manually-filled balloons, the inflation fluid diffuses through the balloon material during the surgical procedure allowing the balloon to partially deflate—even a slight deflation can permit significant losses in both delivery pressure and cardioplegia solution. Typically, the user must re-establish the seal by re-inflating the balloon without an appreciation of the quantity of inflation fluid lost. The user must take care to avoid over-inflating the sealing balloon, whereby the coronary sinus could be damaged. Alternatively, self-filling balloon catheters use the pressure of the infused cardioplegia solution as a means of inflating the sealing balloon. As may be discerned by this method of inflation, self-filling balloons deflate during interruptions or cessations in the delivery of the cardioplegia solution.

Without regard to the type of catheter used, the ability to achieve the necessary level of perfusion is conditioned upon (i) minimizing the quantity of cardioplegia solution "lost" to the human systems and (ii) establishing and maintaining sufficient delivery pressure within the coronary sinus. Since the latter can be dependent upon the former, the primary objective is to limit the opportunity for losses of cardioplegia solution, wherein cardioplegia solution is said to be "lost" when it flows into the right atrium (the region to which the coronary sinus opens).

Cardioplegia solution may reach the right atrium by two primary paths: (i) immediately about the sealing balloon within the coronary sinus (a "backflow" path), and (ii) indirectly about the sealing balloon through the vascular system of the heart (a "shunting" path). Shunting particularly describes the flow of cardioplegia solution from its delivery point, through the interconnecting vessels of the heart, to a plurality of return vessels which open into the coronary sinus immediately adjacent to the coronary sinus ostium. Avoiding these differing means of loss and maintaining the pressure within the coronary sinus is directly related to the ability to establish and maintain an adequate seal between the balloon surface and the vessel wall of the coronary sinus (i.e., to eliminate backflow losses) and position such seal to effectively segregate the coronary sinus proper from the right atrium (i.e., to eliminate shunting losses). Current balloon catheters, when properly positioned and sufficiently inflated, are generally capable of preventing backflow loses; however, such catheters tend to facilitate shunting losses. In theory, conventional balloon catheters can prevent backflow and shunting losses, if positioned in the coronary sinus ostium. Unfortunately, such positioning is not practicable. Shunting results from (i) sealing balloons having a short longitudinal length (as currently practiced by known balloon catheters) and (ii) the practical need to position such balloons deep within the coronary sinus canal to prevent the anticipated displacement of the balloon into the right atrium during the procedure. Accordingly, by placing the sealing balloon deep within the coronary sinus canal, known devices cannot obstruct the plurality of return vessels located near the coronary sinus ostium, thus shunted cardioplegia solution can flow without obstruction from these return vessels into the right atrium.

Illustrating the significance of such losses, at least one study, using self-filling, non-occlusive conventional balloon catheters, found that 35–55% of delivered cardioplegia regurgitated into the right atrium. (Rudis, E., et al., *Coronary Sinus Ostial Occlusion During Retrograde Delivery of Cardioplegic Solution Significantly Improves Cardioplegic Distribution and Efficacy*, 59 THE JOURNAL OF THORACIC AND CARDIOVASCULAR SURGERY 941, 944 (1995). Appreciating the logistical and health consequences associated with such losses (over-exposure of the human system to excessive quantities of cardioplegia solution can lead to the development of a variety of adverse health conditions, including hemodilution and hyperkalemia) as well as the lack of cardioplegia delivered to the right ventricle region of the heart, the study sought to demonstrate the benefits of eliminating backflow and shunting losses.

For the study, an arrant seal was created by surgically occluding the coronary sinus ostium about an inserted balloon catheter. In evaluation of five explanted hearts, the empirical results indicated that such occlusion can virtually eliminate the loss of delivered cardioplegia solution (from 35–55% to 0–1.8% of that delivered, see Rudis, *Ostial Occlusion* at 943, Table 1). Consequently, limiting such losses translated into reduced delivery flow rates and better distribution of cardioplegia throughout the heart. Although exhibiting both impressive and desirous results, the technique requires that the right atrial wall be opened to allow such access to the coronary sinus ostium to permit the application of a purse-string suture, or the like, about the operatively inserted catheter. Simply, the extreme and invasive nature of this procedure is not currently practical for human patients. Notwithstanding, these results lend support to the idea that establishing a near-complete segregation of the coronary sinus from the right atrium, i.e., eliminating both backflow and shunting losses, directly impacts, at least the pressure within the coronary sinus and the extent and efficiency of perfusion.

In practical operation, conventional balloon catheters are susceptible to (i) slippage, wherein the sealing balloon does not effectively maintain its position within the coronary sinus, and (ii) "backing-out," the self-induced, rearward movement of the sealing balloon into the right atrium. In regard to the former, improper inflation, whether due to an initial under-inflation (manually-filled) or losses of inflation fluid during the procedure (manually-filled and self-filling), prevents current devices from firmly holding the catheter, particularly the delivery tip, in a fixed position within the coronary sinus. The sealing balloon should maintain the position of the catheter and be resistant to longitudinal movement within the coronary sinus canal. The avoidance of such movement lessens the opportunity for the catheter to become displaced and also reduces the strain placed upon supporting sutures that often couple the catheter to the heart or other surrounding tissue. Current anti-slippage techniques for conventional sealing balloons are limited to material selection and dependence upon the potentially unreliable form that the balloon assumes upon inflation. In some limited instances, sealing balloons have also been provided with "ribs" along the balloon surface to assist in resisting longitudinal movement.

Backing-out, a particular form of slippage, results from a portion of the sealing balloon being outside the coronary sinus ostium (generally due to improper placement during insertion), whereby the uninhibited portion of the sealing balloon acts to pull the remaining portion of the balloon from the coronary sinus. Although most common during inflation, backing-out may also occur during the open heart procedure. Current manually-filled balloon catheters are more susceptible to backing-out, wherein such devices typically have short, non-rigid sealing balloons that, when utilizing a migratory inflation fluid, creates a seal that conforms to a path of least resistance—such path typically leading a portion of the balloon out through the coronary sinus ostium. Backing-out can be of course overcome by placing the sealing balloon well within the coronary sinus but, as discussed earlier, such placement generally promotes shunting losses.

U.S. Pat. No. 3,799,173 discloses a tracheal tube. The '173 Patent describes a tube having a cuff, such cuff having a sponge-like resilient material being disposed therein. The tracheal tube, as disclosed, operates to feed air, or the like, into and out of the respiratory tract of a patient while maintaining a seal between the cuff and the trachea. The '173 Patent does not, however, suggest a sealing device for a retrograde cardioplegia catheter. Further, the '173 Patent does not suggest the ability to increase the efficacy of cardioplegia delivery to the coronary sinus of a patient's heart, wherein the cardioplegia catheter not only provides a consistent seal between the sealing device and the vessel wall to prevent backflow losses but also prevents shunting, slippage, and backing-out. Instead, the '173 Patent expressly teaches a resilient form which exerts no greater than 25 centimeters of water (0.356 psi) in normal operation. Thus, even if the disclosed tracheal tube were significantly scaled downward to fit within a coronary sinus, although there is no teaching of such within the disclosure, the device as expressly taught would actually promote backflow losses, making such less desirable than conventional balloon catheters.

In light of present methods of delivery of cardioplegia solution in a retrograde direction, a need remains for a retrograde cardioplegia catheter capable of establishing and maintaining an improved seal within the coronary sinus. In part, such improved retrograde cardioplegia catheter must provide a reliable seal, substantially eliminating both backflow and shunting leakage, and effectively hold the catheter securely in place.

SUMMARY OF THE INVENTION

The present invention is directed to a retrograde cardioplegia catheter and its method of use. According to the present invention, a retrograde cardioplegia catheter is disclosed that includes a flexible, elongated cannula having a proximal and a distal end. The cannula includes at least two lumen, the primary lumen being utilized to deliver cardioplegia solution. About the distal end of the cannula, a sealing member is positioned and secured. The sealing member is comprised of (i) a thin-walled membrane that defines an interior chamber and (ii) a compressible, resilient form positioned within such chamber to fully support the membrane. The resilient form is in an expanded state when relaxed. The second of the two lumen extends from a position within the sealing member to a position adjacent to the proximal end of the cannula. Further, the second of the two lumen is in fluid communication with the interior chamber.

An object of the present invention is to provide a retrograde cardioplegia catheter that significantly curtails the loss of delivered cardioplegia solution, whether attributable to backflow or shunting.

Another object of the present invention is to provide a retrograde cardioplegia catheter that creates a sufficient seal within the coronary sinus as to preclude leakage and ensure distribution of cardioplegia solution to all the desired regions of the heart.

Another object of the present invention is to provide a sealing device that possesses a significant longitudinal contact length that, when operatively positioned: enables the occlusion of those return vessels near the coronary sinus ostium that contribute to shunting losses, resists slippage, and permits at least a portion of the sealing balloon to extend outside the coronary sinus without ultimately compromising the established seal.

Another object of the present invention is to provide a sealing device that, when expanded, creates a seal at the sealing device-vessel wall interface via a consistent, safe pressure exerted by the sealing device and a complementary compressive force exerted by the vessel walls of the coronary sinus.

Another object of the present invention is to provide a sealing device that, in conjunction with a supporting suture, acts to prevent unnecessary movement of the catheter within the coronary sinus.

Another object of the present invention is to provide a catheter that is prepared for insertion by drawing a vacuum on, or applying a uniform compressive force to, the sealing device, and then allowing the sealing device to return to its expanded/relaxed state once positioned within the coronary sinus, such expanded state assuming the dimensions of a compressive, resilient form included within the sealing device.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding element throughout the several views:

FIG. 1 is a plan view of one preferred embodiment of a retrograde catheter embodying the principles of the present invention;

FIG. 2 is a longitudinal cross-section of the sealing device of the invention shown in FIG. 1 taken along line 2—2, depicting a relaxed state;

DESCRIPTION OF THE PREFERRED EMBODIMENTS

FIG. 1 illustrates a preferred embodiment of a retrograde cardioplegia catheter 10 for the delivery of a cardioplegia solution to the coronary sinus of a patient's heart during any procedure requiring cardiopulmonary bypass. The catheter 10 is suited for both human and veterinary procedures. The catheter 10 of the present invention effectively segregates the coronary sinus from the right atrium during a retrograde application of cardioplegia solution. Such segregation facilitates, at least: (i) the maintainability of increased pressures within the coronary sinus to allow for the delivery of lower volumetric flows of cardioplegia solution to the patient; (ii) improved distribution of cardioplegia solution throughout all regions of the heart; and (iii) greater efficiency in the delivery of the cardioplegia solution with fewer losses attributable to backflow (the flow of cardioplegia solution around the catheter's sealing device and into the right atrium) or shunting (the flow of cardioplegia solution around a sealing device via a network of interconnecting blood vessels within the heart).

Figure 4:
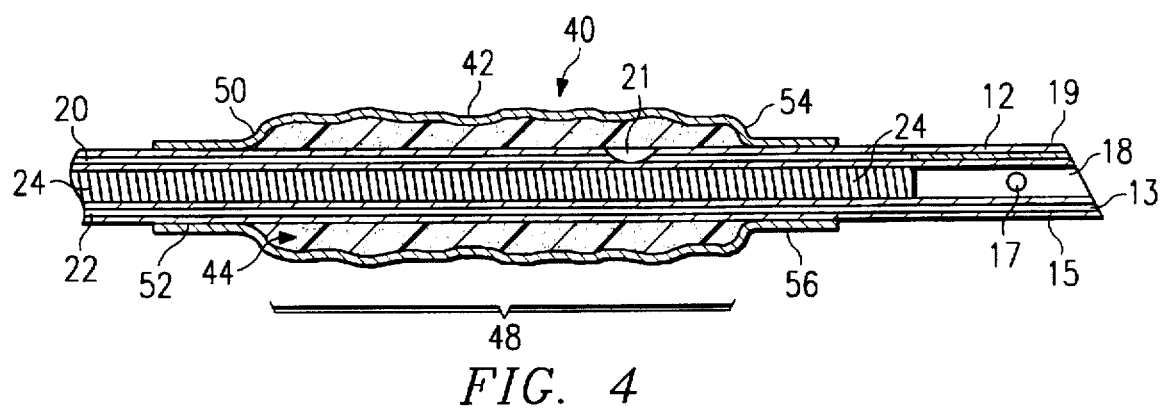
FIG. 4 is a longitudinal cross-section of the sealing device of the invention shown in FIG. 2, depicting a compressed state.
Figure 5:
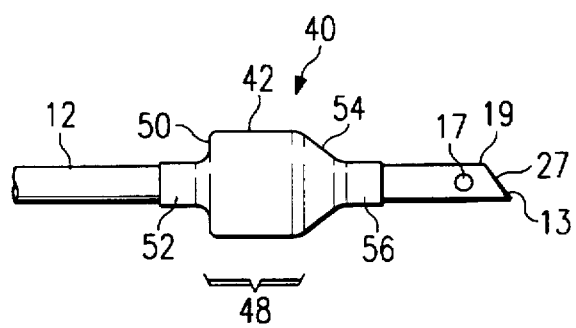
FIG. 5 is a partial side view of an alternative embodiment of the sealing device of the present invention.

In reference to FIGS. 1 and 2, the catheter 10 is generally comprised of a cannula 12 and a sealing device 40. The cannula 12, having a proximal end 14 and a distal end 16, includes a perfusate lumen 18 extending longitudinally through the cannula 12 from the proximal end 14 to the distal end 16. The distal end 16 defines a tip 19 which forms the outlet 27 for the perfusate lumen 18. Within the tip 19, transverse outlets 17 permit the delivery of the cardioplegia solution in the event the outlet 27 becomes obstructed. The tip 19 may assume various shapes, one embodiment is depicted in FIG. 1 and an alternative embodiment is depicted in FIGS. 2, 4, and 5.

The cannula 12 is preferably constructed of medical grade silicone or polyvinylchloride, wherein such material displays consistent flexibility and resiliency characteristics. As shown in FIG. 2, a flexible spring 24, of a diameter corresponding to the diameter of the perfusate lumen 18, may be inserted longitudinally within the perfusate lumen 18. The flexible spring 24 provides both general support and additional rigidity to the cannula 12. The spring 24, while contributing to the usability of the catheter 10, is not essential for the operation of the present invention.

The cannula 12 further includes a second lumen 20 and an optional third lumen 22. The second lumen 20 originates at the proximal end 14 and terminates at a position short of the distal end 16. An aperture 21 defines a passage extending from the exterior surface of cannula 12 to the second lumen 20 at or near the termination location of the second lumen 20 (see FIGS. 2 and 4). In the preferred embodiment, aperture 21 is substantially elliptical with a length approximately twice the diameter of the second lumen 20. Additionally, the third lumen 22 originates at the proximal end 14 and extends to the distal end 16. The third lumen 22 extends through the tip 19 and terminates at port 13, wherein the third lumen 22 further includes at least one addition opening 15 to permit fluid communication between the third lumen 22 and the surrounding environment in the event port 13 becomes obstructed. In the preferred embodiment, the third lumen 22 is used as a means to communicate pressures within the coronary sinus to a pressure-sensing device (not shown) coupled to at least the proximal end 14 of the third lumen 22.

The second and third lumens 20, 22 may be either unitarily molded as elements of the cannula 12 (see FIG. 3) or assembled, using separately formed tubing, using techniques to join the components commonly known to those skilled in the art for the assembly of devices used in medical procedures such as those described herein. Further, the number and placement of lumens and their associated outlets may vary according to the required implementation and the desired functionality of the catheter 10 and is not limited by the configuration of the preferred embodiment.

Positioned at the proximal end 14 is a junction device 26, having a conventional Y-type configuration, which couples the perfusate lumen 18 to a cardioplegia infusion line 28, the second lumen 20 to an extension line 30, and the third lumen 22 to a pressure-sensing line 32. The effect of junction device 26 is to provide fluid communication between the lumen 18, 20, 22 and their respective coupled lines 28, 30, 32 (hereinafter any individual reference to lines 28, 30, 32 or lumens 18, 20, 22 will necessarily infer the respective combination of lumen 18, 20, 22 and lines 28, 30, 32). It should be understood to those skilled in the art that the junction device 26 is not essential to the present invention, wherein each lumen and line pair may be alternatively formed as one continuous fluid line.

As shown in FIG. 1, catheter 10 includes a variety of additional elements as a practical means of using the device. For example, catheter 10 includes a suture ring 34 for placement of a supporting suture, a pinch clamp 35 for inhibiting flow through the cardioplegia infusion line 28, and conventional connection means 36 (for example, locking female Luer-Lok® fittings as shown) for coupling catheter 10 to fluid delivery means, syringes, pressure-measuring devices, or any other like device. Other devices, such as a standard stop cock 38 or a check valve (not shown), may also be coupled to the lines of catheter 10 for the purpose of regulating fluid flow.

Figure 3:
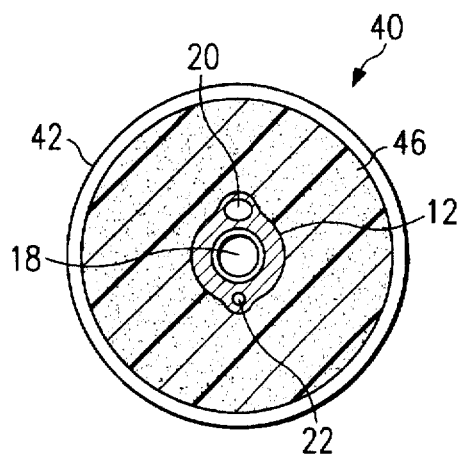
FIG. 3 is a lateral cross-section of the sealing device of the invention shown in FIG. 1 taken along line 3—3 of FIG. 2.

Referring to FIGS. 2 and 3, the sealing device 40, positioned adjacent to the distal end 16, includes a closed membrane 42 and a resilient form 46. The membrane 42 defines an interior chamber 44 which extends from the exterior surface of the cannula 12 to the interior surface of the membrane 42. The resilient form 46 is positioned in the interior chamber 44. The aperture 21, which extends from the exterior surface of the cannula 12 to the second lumen 20, is positioned within the interior chamber 44 to effectively permit fluid communication between the interior chamber 44 and at least the proximal end 14 of the second lumen 20.

The membrane 42 includes a generally cylindrical body portion 48. The body portion 48 defines a contact length, or the longitudinal length of the sealing device 40 that is capable of contacting the vessel wall when in an inserted position. The contact length (i.e., the length of the sealing device 40) may be varied depending upon the circumstances in which the catheter 10 is used or the preferences of the using clinician. The membrane 42 further includes a first end 50 terminating in a first sleeve 52 and a tapered second end 54 terminating in a second sleeve 56, wherein the second end 54 faces toward the distal end 16. The membrane 42 is joined to the cannula 12 at the first and second sleeves 52, 56, wherein the sleeves 52, 56 are hermetically sealed to the exterior surface of the cannula 12. The tapered form of the second end 54, in combination with the flexible tip 19, facilitates easy entry into and safe passage through the coronary sinus canal.

The membrane 42 is unitarily formed from a flexible, fluid-impervious, medical grade material such as silicone or polyurethane. In the preferred embodiment, the membrane 42 is constructed of a silicone material having a thickness ranging from 0.003–0.006 inches and a durometer hardness of 30 on the Shore A scale. It should be understood by one skilled in the art that the selection of material for membrane 42 is determined by a variety of factors, including the dimensions of the sealing device 40, the environment of use, and the procedure to be performed. Consequently, the material defined herein is merely one embodiment and should not be construed as limiting.

An operational attribute of the ultra-thin material of the membrane 42 is repression of wrinkle formation along the surface of the sealing device 40 when such is operatively placed within the coronary sinus. Wrinkles would typically form, if the membrane 42 were made of materials common to known sealing balloons, when the sealing device 40 is positioned within a coronary sinus having an inner diameter smaller than the relaxed dimensions of the sealing device 40. The avoidance of wrinkle-formation is important in avoiding backflow losses, wherein wrinkles assume the form of longitudinal flow channels that permit largely uninhibited flow from the delivery area within the coronary sinus to the right atrium. In comparison, the membrane 42 of the present invention facilitates the formation of a plurality of discontinuous ripples (see generally FIG. 4). The smaller size and discontinuous nature of the ripples preclude the formation of undesired flow channels along the surface of the sealing device 40, thus providing additional safeguards against losses attributable to backflow.

The resilient form 46, as shown in FIG. 2, substantially fills the internal chamber 44 and, in its normal relaxed state, fully supports the membrane 42. The resilient form 46 may comprise a single form or a plurality of annular sections. In one embodiment, the resilient form 46 comprises at least five annular sections, wherein each annular section has a width ranging from 0.0625 to 0.25 inches (the section widths being dependent upon the total length of sealing device 40). The use of a plurality of annular sections improves the longitudinal flexibility of the sealing device 40, thereby facilitating easier movement of the catheter 10 through the heart and coronary sinus canal.

Critical to the invention, the material of the resilient form 46 should exhibit constant compression-relaxation pressure characteristics over a broad use range. In the preferred embodiment, the resilient form 46 is made from a compressible material having compression-relaxation characteristics similar to that depicted in FIG. 6. A material having such characteristics is available from General Foam Company, Paramus, N.J. (part no. 1410a7773). It should be understood by one skilled in the art that the particular material disclosed hereinabove is not a limitation to the present invention but merely one embodiment. Other medical grade materials having low, close hysteresis characteristics and predictable expansion-compression characteristics that exert safe levels of pressure in an expanded state, may equally satisfy the performance requirements of the present invention without departing from the scope of the invention.

Figure 6:
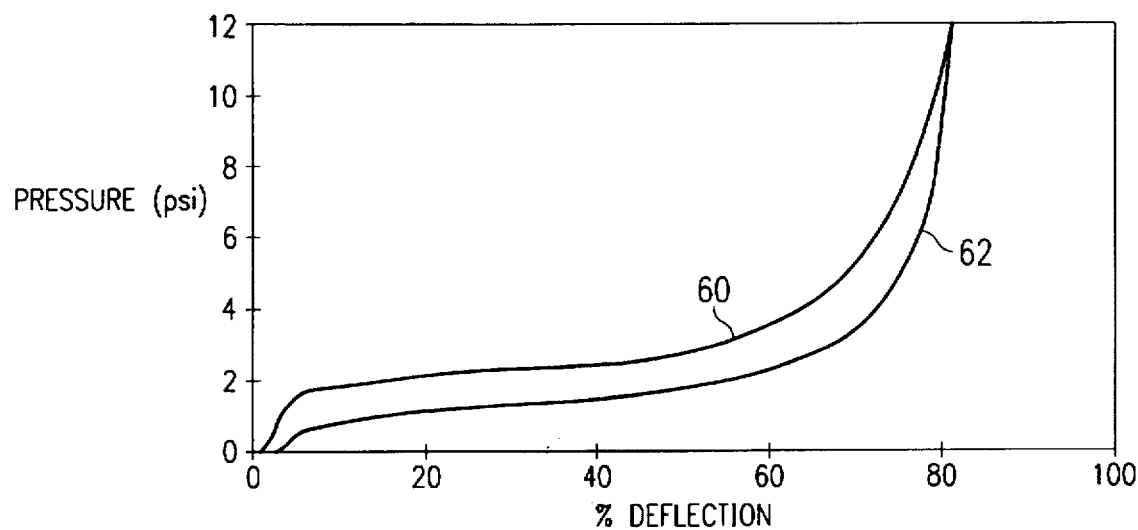
FIG. 6 is a diagram reflecting the compression-relaxation characteristics of the preferred material used to construct the resilient form of the present invention.

Referring to FIG. 6, a typical compression response curve 60 and a typical relaxation response curve 62 for the preferred material is shown. The horizontal axis reflects the percentage deflection of the test material. The vertical axis provides (i) the applied compressive force (compression response curve 60) and (ii) the exerted force of the material (relaxation response curve 62) during relaxation, in pounds per square inch (psi). The response characteristics of FIG. 6 were achieved at a compression-relaxation test rate of ten inches per minute.

From the compression response curve 60, the maximum deflection, or maximum compressed state, of the material occurs at 12 psi. At the maximum compressed state, the preferred material experiences a deflection of substantially 80%. Wherein the material is compressed to a percentage deflection greater than 80%, damage is subject to occur that could subsequently affect the relaxation qualities of the material—particularly, the critical exerted relaxation pressure.

The relaxation response curve 62 illustrates the relaxation characteristics of the preferred material upon the removal of the applied compressive force. The relaxation response curve 62 indicates both the relaxation-transition as well as the measure of the exerted pressure by the material in its return to a relaxed state.

The exerted pressure during relaxation is a critical element in the selection of the resilient form 46 material, wherein sufficient exerted pressure during relaxation is necessary to form an adequate seal between the sealing device 40 and the vessel wall. Care must be taken, however, to avoid excessive pressures that could inadvertently damage the vessel tissue. Generally, inner-vessel pressures of about 50 mm of mercury, or 1 psi, are considered both safe and optimum (although greater pressures could be utilized in other vascular environments). Referring to the relaxation response curve 62, the preferred material exhibits an acceptable exerted pressure in the range of deflection of 0–50%.

As is the nature of the preferred material, the range in which the material exerts pressures at or below 1 psi (0–50% deflection) is consistent with the range ("usable range") of deflection in which relatively constant compression-relaxation pressures are maintainable. In addition to the requirements set forth above, the selected material must be compatible with the operating environment, i.e., the dimensions (e.g., diameter, thickness) of the sealing device 40 and the inner diameter of a coronary sinus, to avoid damage to the coronary sinus by excessive exerted pressures upon relaxation. As an example, referring to FIG. 6, the preferred material would not be acceptable in a scenario where a resilient form possesses dimensions that must undergo 75% deflection for insertion and, due to the inner diameter of a constricted coronary sinus, the material is only allowed to return to a state equivalent to 65% deflection. In this example, the exerted pressure of the material (over 2 psi) exceeds those intravascular pressures considered safe for a coronary sinus.

In consideration of these constraints, the preferred material of the resilient form 46 ensures (i) predictable compression-relaxation ratios throughout the usable range, (ii) an identifiable maximum pressure exerted by resilient form 46, and (iii) that sealing device 40 will consistently move from a compressed state to a relaxed state at an expansion rate consistent with maintaining vessel integrity.

Distinguishable over known balloon catheters, the present invention provides a sealing device 40 that exerts a consistent, uniform distributed force across its surface. Further, unlike the migratory inflation fluids used in known sealing balloons, the resilient form 46 of the present invention provides a necessary degree of rigidity within the sealing device 40 that is not responsive to those conditions that can otherwise compromise the seal of known devices. For example, the seal established by the sealing device 40 is not compromised by its placement in or immediately adjacent to the coronary sinus ostium, such placement providing the inflation fluids of known sealing balloons the opportunity to pull the sealing balloon toward the outlet of the ostium.

In one embodiment, as depicted in FIG. 1, the contact length (i.e., the longitudinal length of the sealing device 40 that is capable of contacting the vessel wall when in an inserted position) of the sealing device 40 measures substantially 1.25 inches. Such length enables the sealing device 40 to effectively eliminate shunting losses by occluding those return vessels positioned near the coronary sinus ostium for a distance equivalent to the contact length of the sealing device 40 (as should be noted, the occlusion of the return vessels does not compromise the perfusion of the right ventricular region, such region receiving cardioplegia solution through the venovenous/venothebesian system of the heart). As another attribute, a contact length of substantially 1.25 inches provides greater resistance to longitudinal movement within the coronary sinus, wherein the exerted force of the resilient form 46 is communicated over a larger surface area. As well, this length/distributed force combination permits a portion of the sealing device 40 to extend from the coronary sinus into the right atrium without compromising the ability to establish a seal. Likewise, once such seal is established, this embodiment of the present invention prevents backing-out of the catheter 10 into the right atrium during the subsequent open heart procedure.

In an alternative embodiment, as depicted in FIG. 5, the contact length measures substantially 0.75 inches, such shorter length being comparable to the length of known sealing balloons. Although this embodiment does not possess all of the attributes of the first embodiment, such remains capable of successfully segregating the coronary sinus from the right atrium. Due to the uniform distribution of force provided by the resilient member 46, the sealing device 40 of the present invention is capable of providing a more reliable and maintainable seal per unit length than known sealing balloons. As discussed, clinicians are often forced to place the short sealing balloon of known catheters deep within the coronary sinus to avoid the displacement of the catheter during the open heart procedure. Consequently, such placement (i) increases shunting losses, and (ii) by the teachings of some, compromises the perfusion of the right portion of the heart. The present invention, however, allows the clinician to position the catheter at the coronary sinus ostium without the fear of displacement or establishing an inadequate seal. As a benefit to such placement, shunting losses are avoided and the efficacy of perfusion is increased. Further, for those who oppose the occlusion of all return vessels near the coronary sinus ostium, the shorter sealing device 40 of the present invention allows delivery of cardioplegia in a manner consistent with such belief.

The average size of a human coronary sinus is determinative of the preferred cross-sectional diameter of the sealing device 40, wherein such diameter measures from 0.70 to 0.75 inches.

In reference to implementation of the present invention, a vacuum device (for example, a syringe) (not shown) is coupled to the extension line 30 via stop cock 38 (it should be noted, that the vacuum device could be connected directly to extension line 30 via connector 39). With stop cock 38 set to an open position ("open" indicating that fluid may freely flow to and from the interior chamber 42 and the ambient environment through an inlet/outlet of the stop cock 38), the vacuum device is initiated and a vacuum is drawn on the sealing device 40. As described hereinabove, the interior chamber 44 and its contents (resilient form 46) are in fluid communication with the second lumen 20 per aperture 21, wherein the applied vacuum acts to reduce the sealing device 40 to a collapsed state by the negative pressure applied to the interior of the membrane 42. Holding the vacuum, stop cock 38 is closed to maintain the collapsed state. Once stop cock 38 is closed, the vacuum device may be removed from the catheter 10 for later use.

In an alternative embodiment, with the stop cock 38 set to an open position, a uniform external compression force is applied directly to sealing device 40 to reduce it to a collapsed state. Holding the sealing device 40 in a collapsed state, stop cock 38 is closed to maintain the collapsed state. For the purpose of this and the following alternative embodiment, the external compressive force may take any variety of forms, including, but not limited to, the rolling of the sealing device 40 between the human thumb and forefinger.

In an alternative embodiment, the extension line 30 is coupled to a standard check valve (not shown) of a conventional duck-bill configuration. With the stop cock 38 set to an open position ("open" indicating a path extending from the interior chamber 44 to the check valve), a uniform external compression force is applied directly to sealing device 40 to reduce it to a collapsed state. Due to the functionality of the check valve allowing air to only exit the interior chamber 44, the sealing device 40 maintains a collapsed state after withdrawal of the uniform compressive force.

Figure 7:
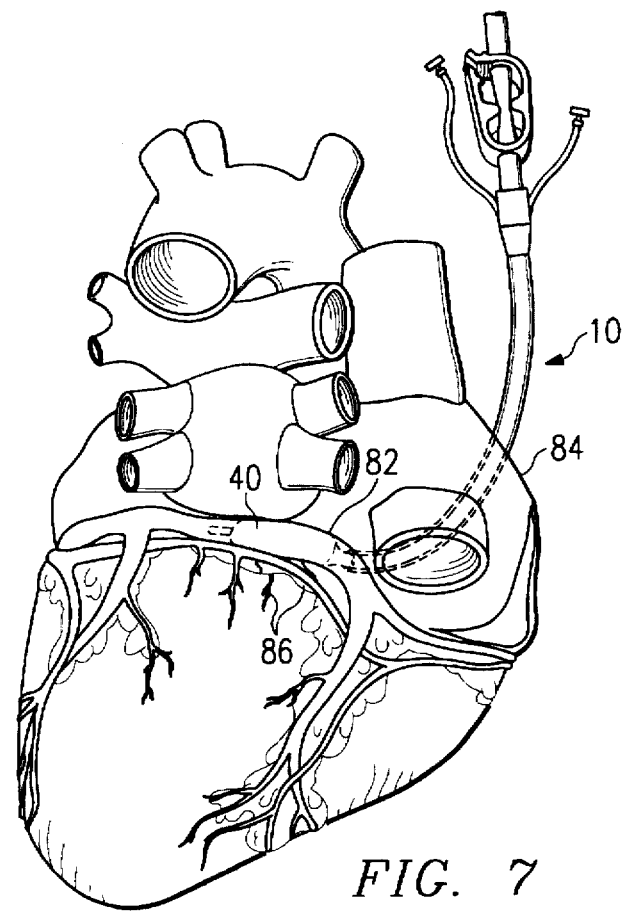
FIG. 7 is a perspective view of the posterior side a patient's heart receiving the present invention.

Referring to FIG. 7, once the sealing device 40 is reduced to a collapsed state, the catheter 10 may be placed within the patient's coronary sinus 82. Specifically, the catheter 10 is advanced, distal end 16 first, through an incision in the patient's right atrial wall 84 and into the coronary sinus 82. The sealing device 40 is positioned entirely within the coronary sinus 82. Although this placement is encouraged, the extended body portion 48 (for the first embodiment) and the operational characteristics of the resilient form 46 are effective in avoiding the backing-out of the device into the right atrium, even if a portion of the sealing device 40 extends into the right atrium.

As with known catheter devices, the symmetrical form of sealing device 40 about the cannula 12 permits consistent, centered placement of the tip 19 within the coronary sinus 82. If using the first embodiment of the catheter 10, wherein the body portion 48 measures substantially 1.25 inches, a properly positioned catheter 10 permits occlusion of the return branches 86 adjacent to the coronary sinus ostium for a distance equivalent to the contact length of the sealing device 40.

The catheter 10 may employ a flexible stylet (not shown) that extends longitudinally through and substantially the length of both the cardioplegia infusion tube 28 and the perfusate line 18. Such stylet permits the catheter 10 to be better controlled during insertion, while not substantially impairing the flexibility of the device.

Once the catheter 10 is positioned, the stop cock 38 is opened and the sealing device 40 allowed to expand to its relaxed state. Once the sealing device 40 is relaxed, a seal is formed between the vessel wall of the coronary sinus 82 and the exterior surface of membrane 42. Common to these procedures, the catheter 10 may be secured at suture ring 34 with a supporting suture (commonly a shared suture with that used to close the incision in the right atrial wall 84). Once the catheter 10 is secured, the stylet is removed.

Regarding the seal, the closed interface between the sealing device 40 and the vessel wall is established by the combination of a uniform, exerted radial pressure from the resilient form 46 and a complementary, compressive force applied by the coronary sinus 82. Unlike known devices that utilize a fluid-filled balloon, the exerted pressure of sealing device 40 is uniform in force distribution due to the material properties and selected geometric shape of the resilient form 46. Moreover, sealing device 40 provides continuous outward pressure until a vacuum is drawn to reduce the sealing device 40 to a collapsed state. Consequently, the established seal of the sealing device 40 is not susceptible to displacement during interruptions in cardioplegia delivery, diffusion of a inflation fluid through the balloon material, or over-inflation.

Returning to the implementation of the device, upon preparing the cardioplegia infusion line 28 and the pressure-sensing line 32, including the coupling of a cardioplegia source (not shown) to infusion line 28 and a pressure transducer (not shown) to pressure-sensing line 32, cardioplegia solution is introduced to the coronary sinus 82 through the cardioplegia infusion line 28. During the delivery of cardioplegia, pressure within the coronary sinus 82 may be monitored at the outlet 13 via the third lumen 22.

Upon completion of the procedure, a vacuum device is recoupled to the extension line 30 and a vacuum drawn to reduce the sealing device 40 to a collapsed state. When the sealing device 40 is collapsed and any necessary sutures removed, the catheter 10 may be safely extracted from the coronary sinus 82.

While the invention has been described herein relative to a number of particularized embodiments, it is understood that modifications of and alternatives to these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein, and it is intended that the scope of the invention disclosed herein be limited only by the broadest interpretation of the appended claims to which the inventors are legally entitled.

We claim:

1. A retrograde cardioplegia catheter comprising:
   (a) a flexible, elongated cannula having a proximal end and a distal end and a first lumen spanning therebetween;
   (b) a sealing member, fixedly coupled to and encompassing the cannula adjacent to the distal end, having a compressible resilient member that allows the sealing member to assume a reduced cross-section when in a compressed state and maintains the sealing member in an expanded position when in a less compressed state; and
   (c) a second lumen, integrally formed with the cannula, originating at the proximal end of the cannula and terminating within the sealing member.

2. The catheter of claim 1, wherein the resilient member is constructed of a compressible, porous material exhibiting consistent force and low hysteresis characteristics.

3. The catheter of claim 1, wherein the sealing member further includes a membrane defining an interior chamber, the resilient member being positioned therein.

4. The catheter of claim 3, wherein the second lumen is in fluid communication with the interior chamber.

5. The catheter of claim 3, wherein the membrane has a thickness of 0.003–0.006 inches.

6. The catheter of claim 1 further comprising a third lumen, integrally formed with the cannula, originating at the proximal end of the cannula and terminating at the distal end of the cannula, the proximal end of the third lumen being coupled to pressure-sensing means.

7. A retrograde cardioplegia catheter for insertion into a patient's coronary sinus, the catheter comprising:
   (a) a flexible, elongated cannula having a proximal end and a distal end and includes a first lumen extending longitudinally between the proximal and distal ends, wherein the distal end defines a tip to which the first lumen extends therethrough;
   (b) a sealing member including,
      (i) a thin membrane, hermetically coupled to and encompassing the cannula adjacent the distal end, having a body portion, first end, and second end that defines an inner chamber between the cannula and the membrane, and
      (ii) a compressible resilient member, received within the inner chamber, that allows the sealing member to assume a reduced cross-section when in a compressed state and supports and maintains the membrane in an expanded position when the resilient member is in a less compressed state, wherein in an inserted position, the sealing member forms a seal within the coronary sinus that substantially prevents a flow of delivered cardioplegia fluid from moving along a natural path from a delivery point in the coronary sinus to the right atrium, and
   (c) a second lumen, integrally formed within the cannula, having a proximal end and a distal end, the distal end terminating within the inner chamber, wherein an aperture in the cannula permits fluid communication between the second lumen and the inner chamber.

8. The catheter of claim 7, wherein the membrane is constructed of thin, flexible, fluid-impervious, medical grade silicone.

9. The catheter of claim 7, wherein the membrane has a thickness between 0.003 and 0.006 inches.

10. The catheter of claim 7, wherein the resilient member is constructed of a compressible, sponge-like microstructure exhibiting consistent force and low hysteresis characteristics.

11. The catheter of claim 10, wherein the microstructure material of the resilient member exhibits a maximum of 80% deflection at 12 psi, and exerts a maximum pressure of substantially 1 psi during relaxation at substantially 50% deflection and less.

12. The catheter of claim 10, wherein the resilient member comprises a plurality of annular sections, each annular section having a thickness between 0.0625 and 0.25 inches.

13. The catheter of claim 7 further comprising a third lumen, integrally formed with the cannula, having a proximal end, such being substantially adjacent to the proximal end of the cannula, and a distal end, such being adjacent the distal end of the cannula, wherein the proximal end of the third lumen is coupled to pressure-sensing means and the distal end of the third lumen extends through the tip of the cannula.

14. The catheter of claim 7, wherein the second end of the membrane is tapered, the second end facing the distal end of the cannula.

15. The catheter of claim 7, wherein the body portion of the membrane has a longitudinal length of at least 0.25 inches.

16. The catheter of claim 7, wherein the sealing member is reduced to a collapsed state for insertion into and withdrawal from the coronary sinus.

17. The catheter of claim 16, wherein the proximal end of the second lumen is adapted to be coupled to a vacuum means, the vacuum means, when initiated, drawing a vacuum upon the sealing member and reducing such to a collapsed state, and further including retention means to maintain such collapsed state.

18. The catheter of claim 16, wherein a uniform, external compression force is applied to the sealing member, reducing such to a collapsed state, and further including retention means to maintain such collapsed state.

19. A method for retrograde delivery of cardioplegia solution for myocardial protection during heart surgery, comprising the steps of:

(a) preparing a patient's heart to receive at least a retrograde catheter, wherein the catheter includes,
  (i) a flexible, elongated cannula having a proximal end and a distal end and includes a first lumen extending longitudinally between the proximal and distal ends, wherein the distal end defines a tip, the first lumen extending therethrough;
  (ii) a sealing members including:
    a thin membrane, hermetically coupled to and encompassing the cannula at a position adjacent the distal end, having a body portion, a first end, and a second tapered end that defines an inner chamber between the cannula and membrane, and
    a resilient member, received within the inner chamber, that allows the sealing member to assume a reduced cross-section when in a collapsed state and supports and maintains the membrane in an expanded position when the resilient member is in a less collapsed state; and
  (iii) a second lumen, integrally formed with the cannula, having a proximal end and a distal end, the distal end terminating within the inner chamber, wherein an aperture in the cannula permits fluid communication between the second lumen and the inner chamber, (b) reducing the sealing member to a first collapsed state to permit entry of the sealing member into a receiving vein within the heart, and engaging a retention means to maintain the first collapsed state;

(c) inserting the sealing member into the receiving vein, wherein the tip enters the receiving vein first, and the receiving vein receives a sufficient portion of the sealing member;

(d) releasing the retention means, allowing the sealing member to return to a relaxed state, wherein a seal is formed by a boundary interface between the membrane and the receiving vein;

(e) delivering cardioplegia solution for at least a portion of the heart surgery, such seal substantially preventing a flow of the delivered cardioplegia fluid from moving along a natural path from a delivery point in the receiving vein to the right atrium;

(f) upon completion of the heart surgery, reducing the sealing member to a second collapsed state to permit withdrawal of the sealing member from the receiving vein, and engaging the retention means to maintain the second collapsed state; and (g) withdrawing the catheter from the patient's heart.

20. The method of claim 19, wherein the first collapsed state and second collapsed state is achieved by coupling the proximal end of the second lumen to a vacuum means and drawing a vacuum on the sealing member.

21. The method of claim 19 wherein the first collapsed state is achieved by application of a uniform, external compression force to the sealing member, and the second collapsed state is achieved by coupling the proximal end of the second lumen to a vacuum means and drawing a vacuum on the sealing member.

22. The method of claim 19, wherein the body portion of the membrane has a longitudinal length of at least 0.25 inches.

23. The method of claim 19, wherein the membrane has a thickness between 0.003 and 0.006 inches.

24. The method of claim 19, wherein the resilient member is constructed of a compressible, sponge-like microstructure exhibiting consistent force and low hysteresis characteristics.

25. The catheter of claim 24, wherein the microstructure material of the resilient member exhibits a maximum of 80% deflection at 12 psi, and exerts a maximum pressure of substantially 1 psi during relaxation at substantially 50% deflection and less.

26. The catheter of claim 25, wherein the resilient member comprises a plurality of annular sections, each annular section having a thickness between 0.0625 and 0.25 inches.

* * * * *